US00PP26930P2

(12) United States Plant Patent
Wood

(10) Patent No.: US PP26,930 P2
(45) Date of Patent: Jul. 12, 2016

(54) ***HYDRANGEA* PLANT NAMED 'SMNHMDD1'**

(50) Latin Name: *Hydrangea macrophylla*
Varietal Denomination: SMNHMDD1

(71) Applicant: Timothy D. Wood, Spring Lake, MI (US)

(72) Inventor: Timothy D. Wood, Spring Lake, MI (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 14/544,630

(22) Filed: Jan. 23, 2015

(51) Int. Cl.
*A01H 5/02* (2006.01)

(52) U.S. Cl.
USPC ..... Plt./250

(58) Field of Classification Search
USPC ..... Plt./226, 250
See application file for complete search history.

*Primary Examiner* — Susan McCormick Ewoldt
*Assistant Examiner* — Karen Redden
(74) *Attorney, Agent, or Firm* — C. A. Whealy

(57) ABSTRACT

A new and distinct cultivar of *Hydrangea* plant named 'SMNHMDD1', characterized by its compact, upright, outwardly spreading and mounding plant habit; strong and sturdy stems; thick dark green-colored leaves; lacecap-type inflorescences with double-type sterile flowers and numerous fertile flowers; and sterile flowers that are bright pink in color.

2 Drawing Sheets

Botanical designation: *Hydrangea macrophylla.*
Cultivar denomination: 'SMNHMDD1'.

BACKGROUND OF THE INVENTION

The present invention relates to a new and distinct *Hydrangea* plant, botanically known as *Hydrangea macrophylla* and hereinafter referred to by the name 'SMNHMDD1'.

The new *Hydrangea* plant is a product of a planned breeding program conducted by the Inventor in Grand Haven, Mich. The objective of the breeding program was to develop new compact and reblooming *Hydrangea* plants with strong stems and attractive inflorescences.

The new *Hydrangea* plant originated from an open-pollination in July, 2007 of *Hydrangea macrophylla* 'Harbits', disclosed in U.S. Plant Pat. No. 21,186, as the female, or seed parent and an unknown selection of *Hydrangea macrophylla*, as the male, or pollen, parent. The new *Hydrangea* plant was discovered and selected by the Inventor as a single flowering plant from within the progeny of the stated open-pollination in a controlled environment in Grand Haven, Mich. in July, 2009.

Asexual reproduction of the new *Hydrangea* plant by softwood cuttings in a controlled environment in Grand Haven, Mich. since July, 2009 has shown that the unique features of this new *Hydrangea* plant are stable and reproduced true to type in successive generations of asexual reproduction.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SMNHMDD1'. These characteristics in combination distinguish 'SMNHMDD1' as a new and distinct *Hydrangea* plant:

1. Compact, upright, outwardly spreading and mounding plant habit.
2. Strong and sturdy stems.
3. Thick dark green-colored leaves.
4. Lacecap-type inflorescences with double-type sterile flowers and numerous fertile flowers.
5. Sterile flowers that are bright pink in color.

Plants of the new *Hydrangea* differ from plants of the female parent, 'Harbits', in the following characteristics:

1. Plants of the new *Hydrangea* have stronger stems than plants of 'Harbits'.
2. Leaves of plants of the new *Hydrangea* are glossier than leaves of plants of 'Harbits'.
3. Sterile flowers of plants of the new *Hydrangea* are double-types whereas sterile flowers of plants of 'Harbits' are single-types.
4. Sterile flowers of the new *Hydrangea* and 'Harbits' differ in color as sterile flowers of 'Harbits' are white and red purple bi-colored.

Plants of the new *Hydrangea* can be compared to plants of *Hydrangea macrophylla* 'SMNHMP1', disclosed in U.S. Plant Pat. No. 25,900. In side-by-side comparisons, plants of the new *Hydrangea* differed primarily from plants of 'SMHMP1' in inflorescence form as plants of the new *Hydrangea* had lacecap-type inflorescences whereas plants of 'SMHMP1' had mophead-type inflorescences.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet comprises a top perspective view of typical flowering plants of 'SMNHMDD1' grown in containers.

The photograph on the second sheet is a close-up view of a typical flowering plant of 'SMNHMDD1'.

DETAILED BOTANICAL DESCRIPTION

Plants used for the aforementioned photographs and the following description were grown during the summer in three-gallon containers in a polypropylene-covered shadehouse in Grand Haven, Mich. and under cultural practices typical of commercial *Hydrangea* production. During the production of the plants, day temperatures ranged from 18° C. to 27° C. and night temperatures ranged from 5° C. to 10° C. Plants of the new *Hydrangea* were two years old when the photographs and description were taken. Plants were overwintered in a polyethylene-covered greenhouse. Plants were not treated with aluminum sulfate. During the production of the plants, the soil pH ranged from 5.0 to 6.0. In the following description, color references are made to The Royal Horticultural Society Colour Chart, 1995 Edition, except where general terms of ordinary dictionary significance are used.

Botanical description: *Hydrangea macrophylla* 'SMNHMDD1'.

Parentage:

*Female, or seed, parent.*—*Hydrangea macrophylla* 'Harbits', disclosed in U.S. Plant Pat. No. 21,186.

*Male, or pollen, parent.*—Unknown selection of *Hydrangea macrophylla*, not patented.

Propagation:

*Type cutting.*—By softwood cuttings.

*Time to initiate roots, summer.*—About 18 days at temperatures about 27° C.

*Time to produce a rooted young plant, summer.*—About 60 days at temperatures about 27° C.

*Root description.*—Fine to thick; white and brown in color.

*Rooting habit.*—Freely branching; dense.

Plant description:

*Plant form and growth habit.*—Perennial deciduous shrub; compact, upright, outwardly spreading and mounding plant habit; strong and sturdy lateral branches; freely branching habit with about 28 lateral branches developing per plant; vigorous growth habit.

*Plant height.*—About 44 cm.

*Plant diameter or area of spread.*—About 72 cm.

*Lateral branches.*—Length: About 30 cm. Diameter: About 1.2 cm. Internode length: About 2 cm to 4 cm. Texture: Smooth, glabrous. Strength: Strong, sturdy. Aspect: Erect to about 45° from vertical. Color, developing and developed: Close to 143A.

Leaf description:

*Arrangement.*—Opposite, simple.

*Length.*—About 7.5 cm to 12 cm.

*Width.*—About 4 cm to 6 cm.

*Shape.*—Ovate.

*Apex.*—Acute.

*Base.*—Cuneate.

*Margin.*—Serrate.

*Texture, upper and lower surfaces.*—Smooth, glabrous; thick.

*Venation pattern.*—Pinnate.

*Color.*—Developing leaves, upper surface: Close to 137A. Developing leaves, lower surface: Close to 146B. Fully expanded leaves, upper surface: Close to 137A; venation, close to 146C. Fully expanded leaves, lower surface: Close to 146B; venation, close to 146D.

*Petioles.*—Length: About 7 mm to 25 mm. Diameter: About 3 mm to 4 mm. Texture, upper and lower surfaces: Smooth, glabrous. Color, upper and lower surfaces: Close to 146B.

Flower description:

*Flower type and habit.*—Double-type sterile and single-type fertile flowers arranged on terminal lacecap cymes that are roughly hemispherical in shape.

*Fragrance.*—None detected.

*Natural flowering season.*—Plants flower throughout the summer in Grand Haven, Mich.; flowers not persistent.

*Quantity of flowers.*—Freely flowering habit; about 630 fertile flowers and about 9 to 14 sterile flowers developing per inflorescence.

*Inflorescence height.*—About 7 cm.

*Inflorescence diameter.*—About 16.5 cm.

*Flower diameter, fertile flowers.*—About 5 mm.

*Flower depth (height), fertile flowers.*—About 7 mm.

*Flower diameter, sterile flowers.*—About 4 cm.

*Flower depth (height), sterile flowers.*—About 3 cm.

*Flower buds, fertile and sterile flowers.*—Length: About 3 mm. Diameter: About 2 mm. Shape: Obovate. Color: Close to 145B and 73B.

*Petals, fertile flowers.*—Quantity and arrangement: About two to five in a single whorl. Length: About 3 mm. Width: About 2 mm. Shape: Ovate. Apex: Acute. Base: Cuneate. Margin: Entire. Texture, upper and lower surfaces: Smooth, glabrous. Color: When opening, upper and lower surfaces: Close to 70B. Fully opened, upper surface: Close to 74D; color becoming closer to 74C with development. Fully opened, lower surface: Close to 75B; color becoming closer to 75A with development.

*Petals, sterile flowers.*—Quantity and arrangement: About 14 in about two whorls. Length: About 2.9 mm. Width: About 2.2 mm. Shape: Ovate. Apex: Obtuse. Base: Cuneate. Margin: Entire; slightly undulate. Texture, upper and lower surfaces: Smooth, glabrous; satiny. Color: When opening, upper surface: Close to 70D; striations, close to 70B. When opening, lower surface: Close to 69A; striations, close to 70B. Fully opened, upper surface: Close to 75A; with development, color becoming closer to 75B to 75C and towards the base, close to 75D. Fully opened, lower surface: Close to 75B to 75C and towards the base, close to 75D; color does not change with development.

*Sepals, sterile flowers only.*—Quantity and arrangement: About eight to ten in about two whorls. Length: About 1.5 cm to 2 cm. Width: About 8 mm to 16 mm. Shape: Elliptic to obovate, unguiculate. Apex: Obtuse. Base: Cuneate. Margin: Entire. Texture, upper and lower surfaces: Smooth, glabrous. Color: When opening, upper surface: Close to 145C and 64D. When opening, lower surface: Close to 62A and 150D. Fully opened, upper surface: Close to 70B; with development, color becoming closer to 75B to 75C and close to 75D towards the base. Fully opened, lower surface: Close to 70C; with development, color becoming closer to 75B to 75C and close to 75D towards the base.

*Pedicels, fertile flowers*.—Length: About 4 mm. Diameter: About 1 mm. Angle: Mostly upright. Strength: Strong, sturdy. Texture: Smooth, glabrous. Color: Close to 70B.

*Pedicels, sterile flowers*.—Length: About 2.5 cm. Diameter: About 2 mm. Angle: Upright to outwardly. Strength: Strong, sturdy. Texture: Slightly pubescent. Color: Close to 64C.

*Reproductive organs, observed on fertile flowers only*.—Stamens: Quantity per flower: If present, about three. Filament length: About 2 mm. Anther shape: Round. Anther length: About 1 mm. Anther color: Pale yellow. Pollen amount: None observed. Pistils: Pistil quantity per flower: One, three-lobed. Pistil length: About 2 mm. Stigma shape: Oblong. Stigma color: Close to 59A. Style length: About 5 mm. Style color: Close to 59A. Ovary color: Close to 155B.

*Seeds and fruits*.—To date, seed and fruit development have not been observed on plants of the new *Hydrangea*.

Temperature tolerance: Plants of the new *Hydrangea* have been observed to tolerate temperatures ranging from about −23° C. to about 35° C.

Disease & pest resistance: Plants of the new *Hydrangea* have been observed to be resistant to Mildew. Plants of the new *Hydrangea* have not been observed to be resistant to pests and other pathogens common to *Hydrangea* plants.

It is claimed:

1. A new and distinct *Hydrangea* plant named 'SMNHMDD1' as illustrated and described.

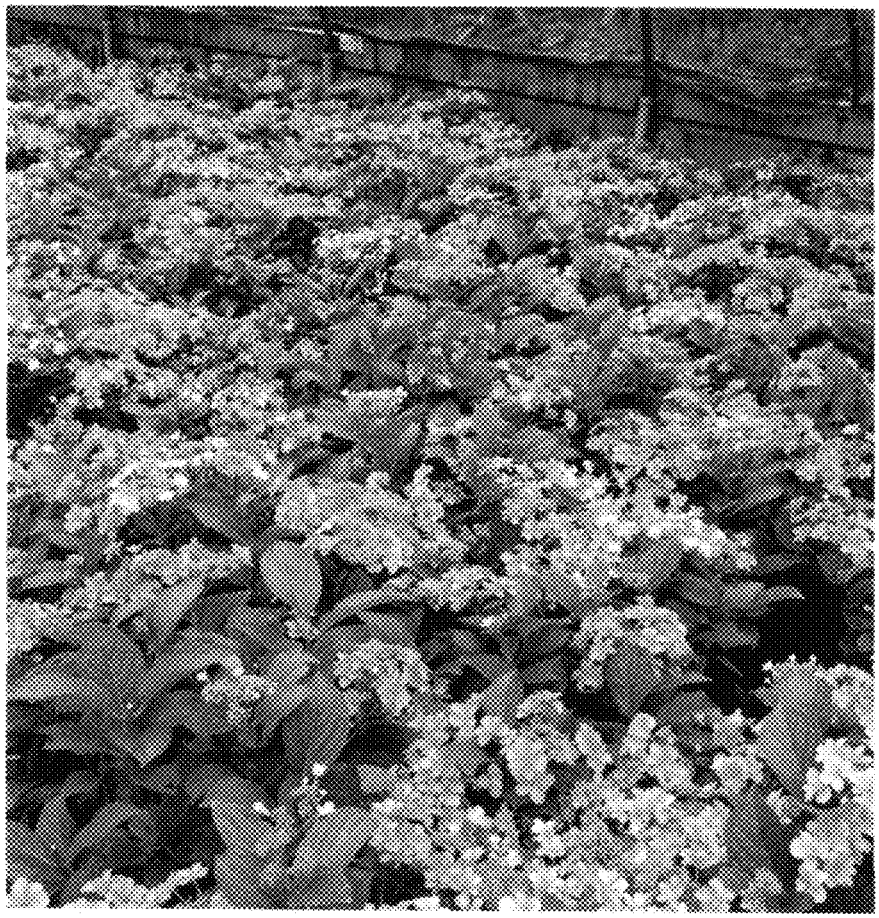

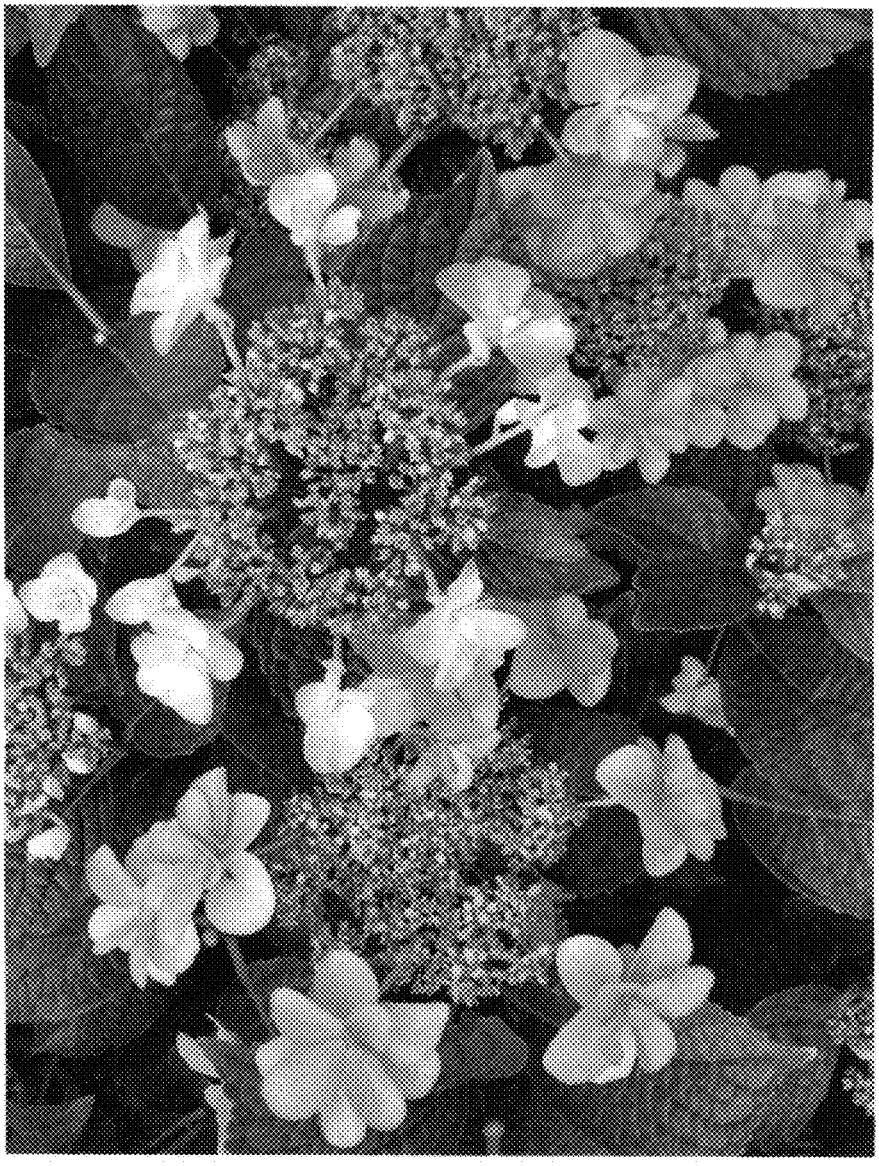

* * * * *